Figure 1:
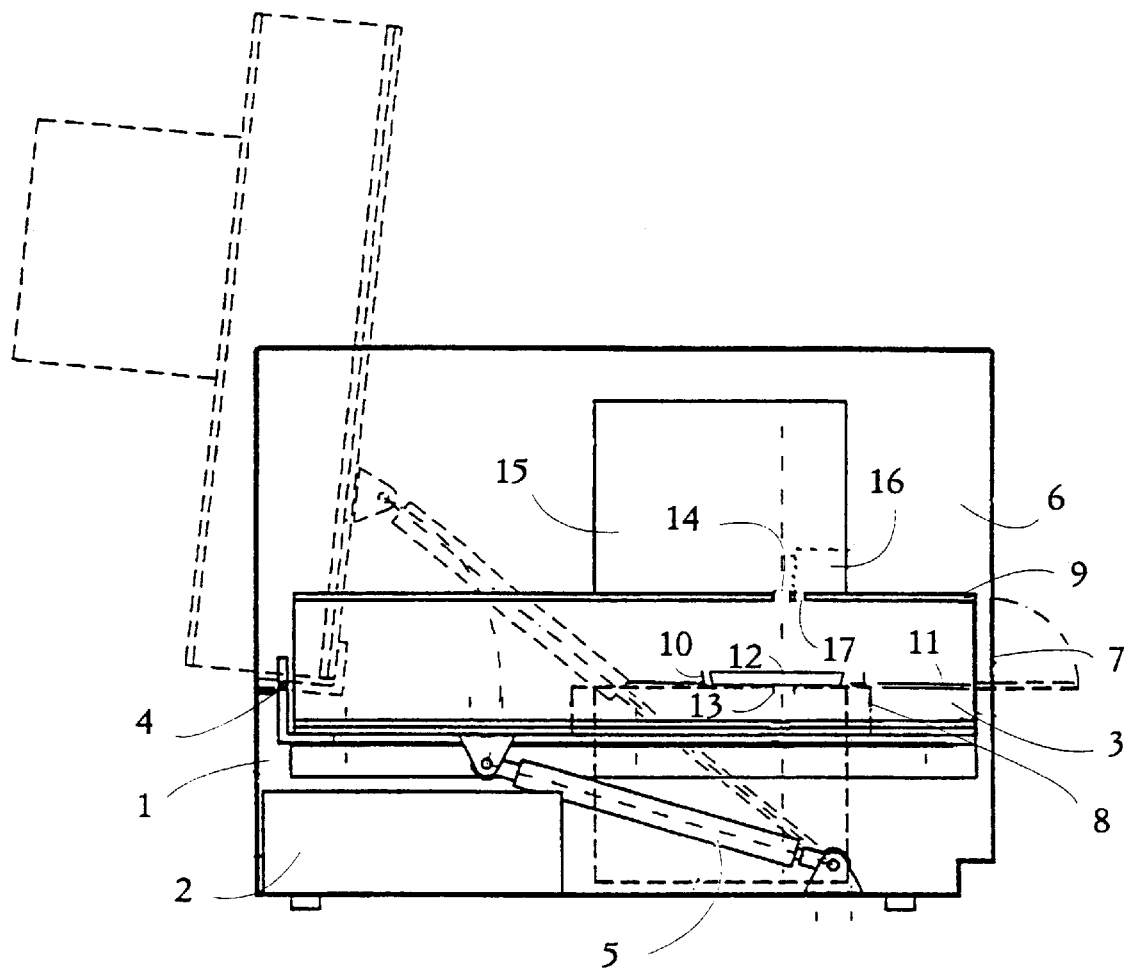

United States Patent [19]
Tuunanen et al.

[11] Patent Number: 6,084,680
[45] Date of Patent: *Jul. 4, 2000

[54] OPTICAL ANALYZER

[75] Inventors: Jukka Tuunanen, Helsinki; Matti Priha, Vantaa; Heikki Tupakka; Timo Kärmeniemi, both of Helsinki, all of Finland

[73] Assignee: Labsystems Oy, Helsinki, Finland

[ * ] Notice: This patent issued on a continued prosecution application filed under 37 CFR 1.53(d), and is subject to the twenty year patent term provisions of 35 U.S.C. 154(a)(2).

[21] Appl. No.: 09/043,323

[22] PCT Filed: Sep. 20, 1996

[86] PCT No.: PCT/FI96/00497

§ 371 Date: Mar. 20, 1998

§ 102(e) Date: Mar. 20, 1998

[87] PCT Pub. No.: WO97/11351

PCT Pub. Date: Mar. 27, 1997

[30] Foreign Application Priority Data

Sep. 22, 1995 [FI] Finland ..................................... 954510

[51] Int. Cl.[7] .......................... G01N 21/01; G01N 21/64
[52] U.S. Cl. ....................................... 356/417; 250/458.1
[58] Field of Search ..................................... 356/317, 318, 356/417, 344; 250/458.1, 459.1, 461.1, 461.2; 422/52, 82.07, 82.08, 942; 436/172

[56] References Cited

U.S. PATENT DOCUMENTS

| | | |
|---|---|---|
| 3,421,821 | 1/1969 | Alessi . |
| 4,053,235 | 10/1977 | Hampton et al. . |
| 4,426,154 | 1/1984 | Steen ......................................... 356/73 |
| 4,501,970 | 2/1985 | Nelson .................................... 356/318 |
| 4,945,250 | 7/1990 | Bowen et al. ........................ 250/461.1 |
| 5,091,652 | 2/1992 | Mathies et al. ....................... 250/458.1 |
| 5,108,179 | 4/1992 | Myers ..................................... 356/344 |
| 5,147,609 | 9/1992 | Grenner .................................... 422/58 |
| 5,360,523 | 11/1994 | Middendorf et al. ................... 356/344 |
| 5,515,169 | 5/1996 | Cargill et al. ........................... 356/417 |

FOREIGN PATENT DOCUMENTS

| | | | |
|---|---|---|---|
| 0 521 636 A1 | 1/1993 | European Pat. Off. ........ | G01N 21/64 |
| 145176 | 10/1981 | Norway .......................... | G01N 21/01 |
| 2 088 580 | 6/1982 | United Kingdom .............. | G01J 3/00 |
| 2 196 734 | 5/1988 | United Kingdom ........... | G01N 21/64 |
| WO 82/00356 | 2/1982 | WIPO ............................. | G01N 21/01 |
| WO 82/00361 | 2/1982 | WIPO ............................. | G01N 21/27 |
| WO 83/00931 | 3/1983 | WIPO ............................. | G01N 35/02 |
| WO 92/22801 | 12/1992 | WIPO ............................. | G01N 21/01 |

*Primary Examiner*—F. L. Evans
*Attorney, Agent, or Firm*—Fish & Richardson P.C.

[57] ABSTRACT

An optical analyzer measures light directed from a sample to the detector. The apparatus has an optics module which has a detector and optics for directing light emitted by the sample to the detector and which module can be positioned alternatively either so that the light is directed to the detector from above the sample or so that light is directed to the detector from below the sample. The invention is usable in particular in fluorometers and in luminometers.

26 Claims, 6 Drawing Sheets

OPTICAL ANALYZER

FIELD OF TECHNOLOGY

The invention relates to instrument technology and concerns optical analysers used in laboratories, in which analysers measuring light is directed from a sample to the detector. Analysers according to the invention can be used, for example, in assays of clinical chemistry and food technology. The invention is particularly suited for use in fluorometers and luminometers.

BACKGROUND

Determinations based on the measurement of the optical properties of a sample are in laboratories usually carried out on plates having a plurality of reaction wells. Photometric measuring is in such a case best performed through the plate in the vertical direction. The measuring light is directed to the plate either from above or from below (cf., for example, WO-82/00356).

Fluorometric measurement through a plate is not particularly recommendable, since in such a case there travels through the plate also a large amount of excitation light, which complicates the measuring of emitted light. In addition, background fluorescence possibly due to the material of the plate constitutes a problem. In most present-day fluorometers available for routine assays, excitation light is directed to the plate from above, and also emitted radiation is collected from above.

In luminometers, the light emitted from the sample is in general directed to the detector from above.

In certain fluorometric assays, the sample is inhomogeneous so that the concentration of the analyte being measured is highest at the bottom of the plate well. This is especially the case in certain samples containing cell cultures. In such a case it would usually be best to direct both the excitation light to the sample and the emitted light from the sample through the bottom of the plate, in order that the solution above the bottom layer should not disturb the measuring.

There are known fluorometers in which the measuring can be carried out either from above or from below (e.g. Series 7600 Microplate Fluorometer, Cambridge Technology, Inc., USA). In such an apparatus the source of light and the detector are fixedly mounted. Excitation light is directed from the source of light to the plate and emitted light is directed from the plate to the detector by means of optical-fiber bundles. The end of a fiber bundle may be placed either above or below the plate. One problem in these apparatuses is the high price of the fiber optics suitable for the purpose.

DESCRIPTION OF THE INVENTION

General description

An improved analyser for measuring optical properties of a sample has now been invented. Preferred embodiments of the invention are stated in the other claims.

According to the first independent characteristic of the invention, the apparatus has, placeable either above or below the sample, an optics module having a detector for the measuring of the light emitted from the sample. Thus the apparatus can be used for carrying out the measuring either from above or from below, depending on the need. However, the apparatus does not require fiber optics for directing light to the detector, since the necessary optical means constitute part of the movable module and can thus be mounted fixedly in relation to the detector.

The apparatus may be, for example, a fluorometer, luminometer, nephelometer, photometer, or any combination of these.

In general the apparatus also has a source of light for directing light to the sample. In practice, apparatuses which are solely luminometers do not need a source of light. The source of light may be separate from the optics module and capable of being mounted either above or below the sample.

Preferably the source of light is part of the optics module. This feature is especially well suited for fluorometers. In this case both excitation light to the sample and emitted light from the sample are directed on the same side of the sample. Precisely in fluorometers, in which the fiber optics usable within the UV range is especially expensive, the avoiding of fiber optics is a particular advantage. Fiber optics also causes background fluorescence, which is thus avoided according to the invention.

The source of light used is preferably an incandescent bulb, if sufficiently short-wave radiation suitable for the purpose can be produced by it.

The source of light may also be made replaceable. In special cases the source of light in the optics module can be replaced with optics by means of which the light is introduced into the module from the outside.

According to another independent characteristic of the invention, the analyser may have an aperture for delimiting the light to be measured and optical means for forming an image of the delimited area of the sample in the aperture. Preferably the size or shape of the delimiting aperture can be varied, in which case measuring light can always be collected from an area of the desired type. Preferably these optical means include a lens system for converging the light emitted by the sample, a mirror to which the converged beam of light is directed, and a converging lens system for forming in the aperture of the delimiter an image of the light reflected from the mirror.

If a filter is used for delimiting to the desired range the wavelength range of the measuring light, the filter is preferably placed at a point after the delimiting aperture. The filtering is preferably performed on collimated light.

According to a third independent characteristic of the invention, the analyser may have means for eliminating errors caused by variations in the distance to the object being assayed. The means include a lens system for collimating the measuring light and a delimiter for delimiting out from the beam of light any scattered rays.

The apparatus is preferably such that samples in different types of vessels can be measured in it. The sample vessels usually constitute a unit made up of a plurality of vessels, such as a microtiter plate. Preferably the apparatus has a movable measurement frame by means of which each sample in turn is taken to the measurement position. By suitable moving of the frame the samples can, when so desired, also be agitated. So-called scanning measuring can also be performed by moving the frame.

DRAWINGS

The accompanying drawings constitute part of the description of the invention. In them

Figure 2:
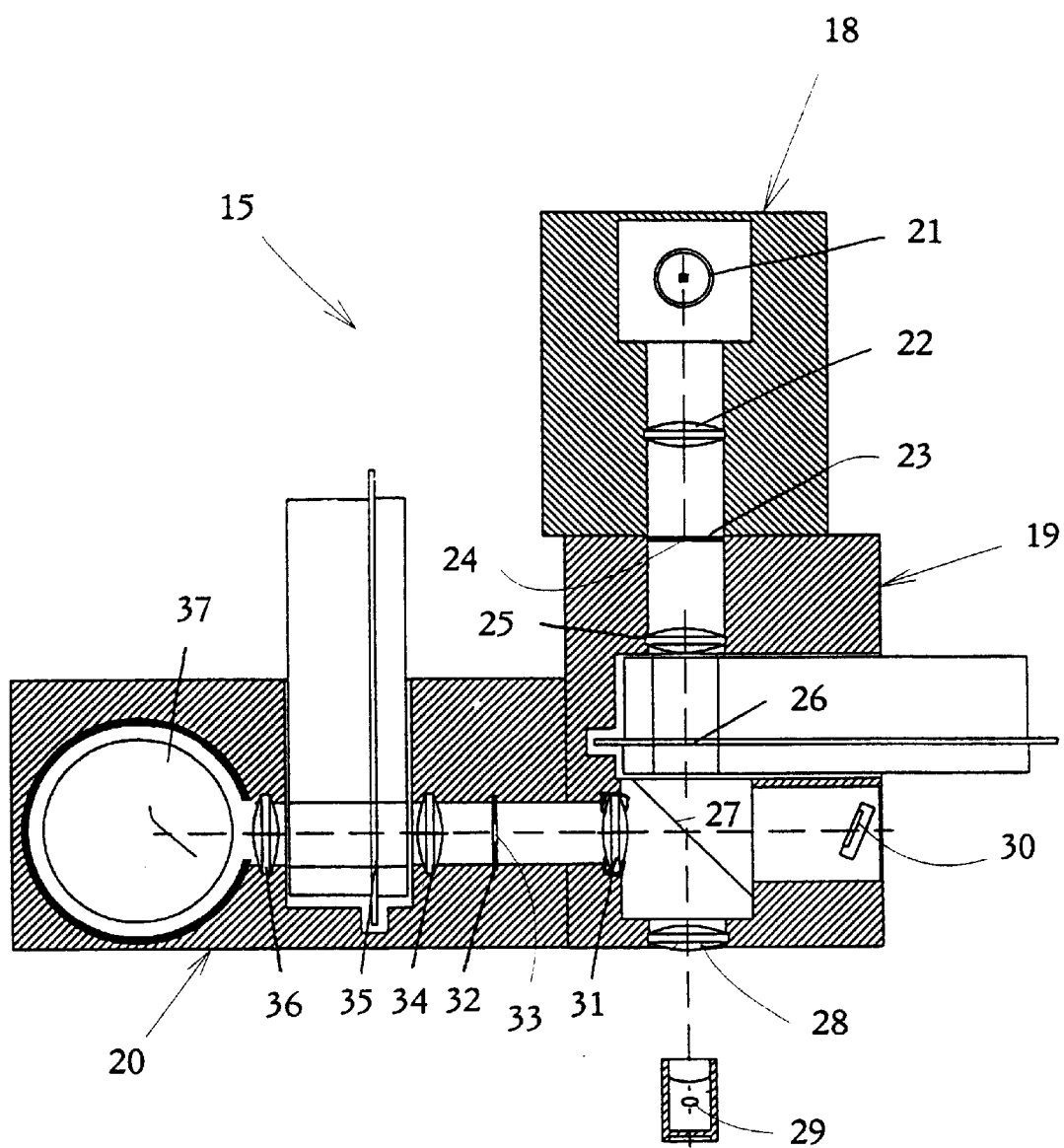
Figure 3:
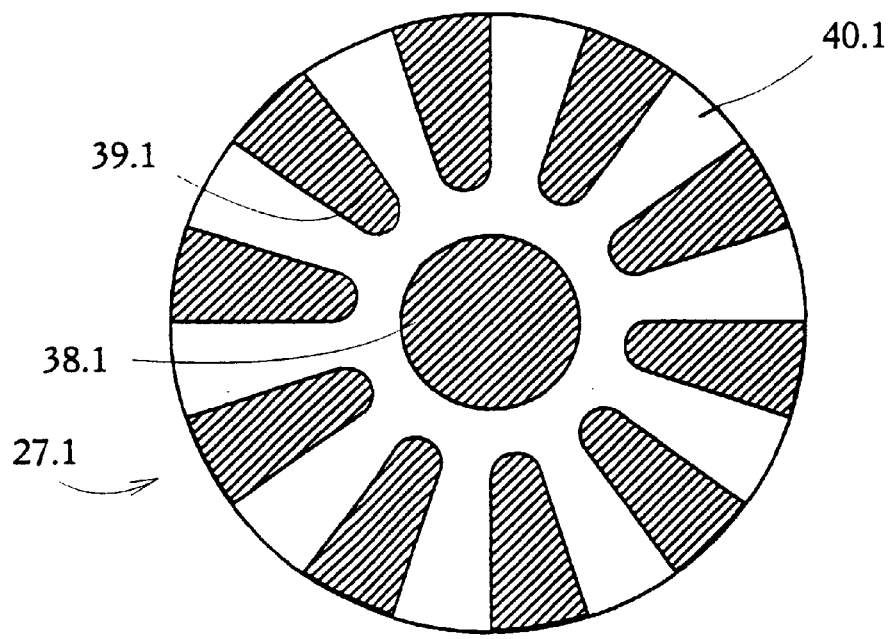
Figure 4:
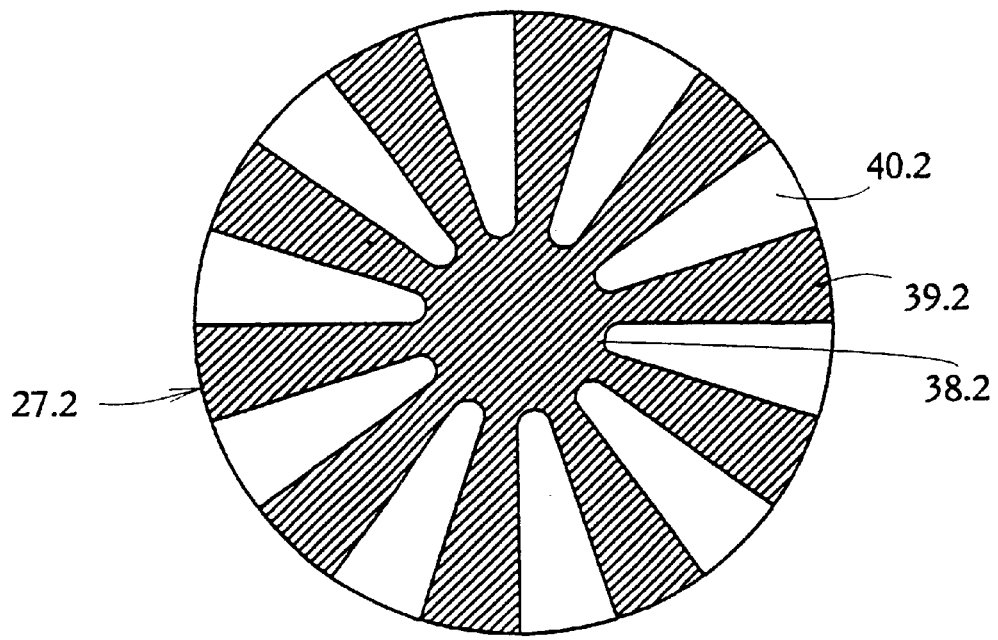

| | |
|---|---|
| FIG. 1 | depicts a side view of one fluorometer according to the invention, |
| FIG. 2 | depicts the optics arrangement of the fluorometer of FIG. 1, |
| FIG. 3 | depicts one mirror usable in the optics arrangement, |
| FIG. 4 | depicts another mirror usable in the optics arrangement, |

Figure 5:
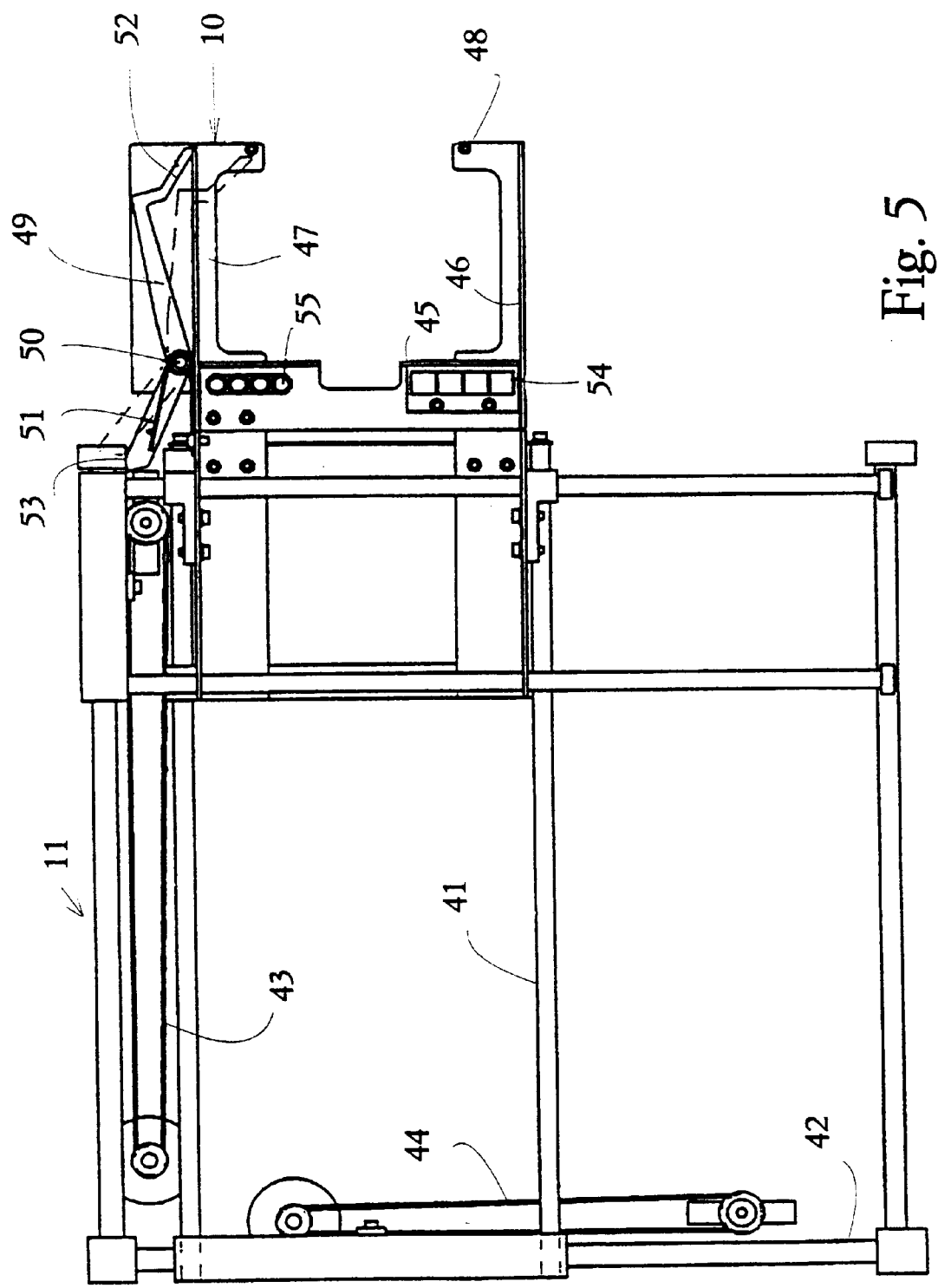
Figure 6:
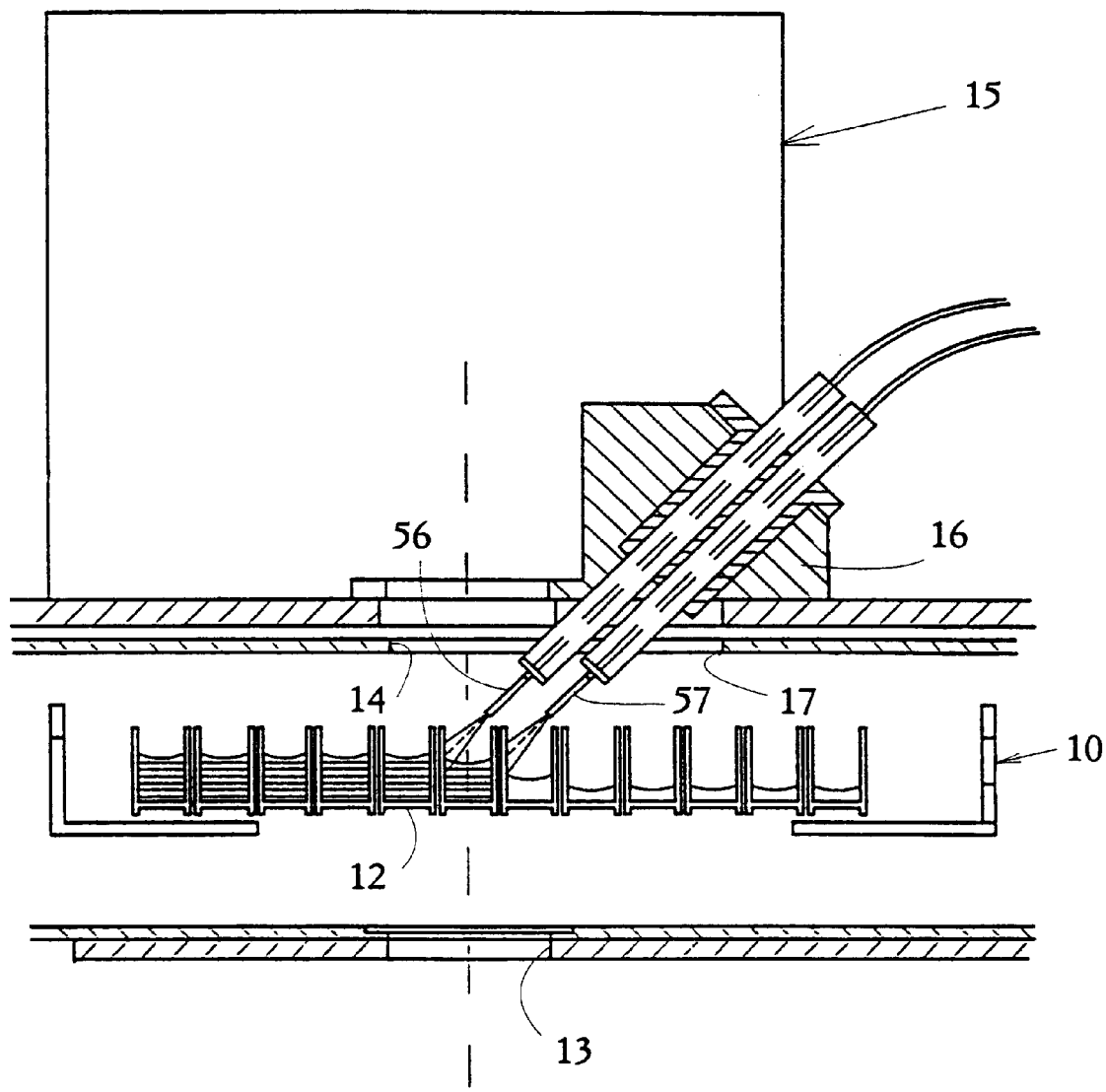
Figure 7:
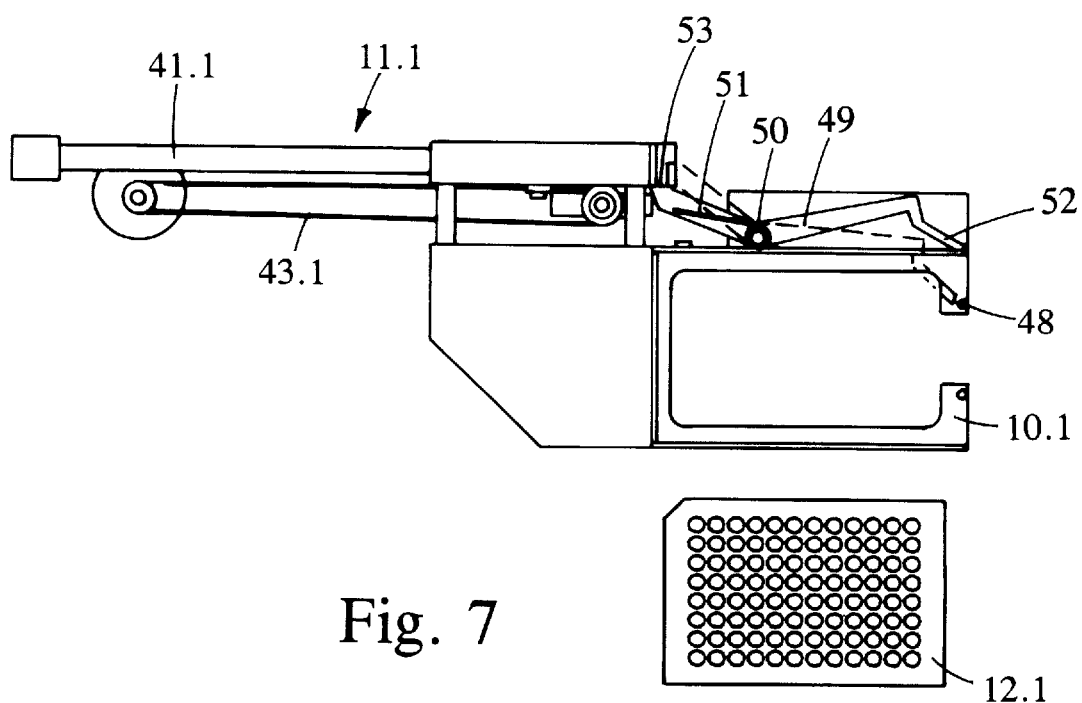

| | -continued |
|---|---|
| FIG. 5 | depicts a plan view of the sample plate transfer system of the fluorometer of FIG. 1, |
| FIG. 6 | depicts a detail of the fluorometer of the figure, having a plate in the dispensing and measuring position, and |
| FIG. 7 | depicts a plan view of another transfer arrangement. |

SPECIFIC DESCRIPTION

The fluorometer of FIG. 1 has a lower housing 1 which houses, among other things, a control unit 2 and connections to the source of power and to functions external to the apparatus. On top of the lower housing there is a light-tight measuring unit 3. Its back edge is hinged 4 to the back edge of the lower housing so that the measuring unit can be pivoted upwards, whereupon there will be easy access to parts below it. The pivoted measuring unit is held in the upper position (shown by dotted lines in FIG. 1) by a pneumatic spring 5. Above the lower housing and the measuring unit there is a detachable upper housing 6. In the front wall of the measuring unit and the upper housing there is an aperture 7 equipped with a light-tight hatch, through which aperture samples are transferred into the measuring unit and out of it.

The measuring unit 3 has a lower deck 8 and an upper deck 9. In the space between these, a measuring carrier 10 is moved by transfer means 11. The plate 12 with the samples to be assayed is placed in the measuring carrier. The measuring carrier can be moved out through the aperture 7.

In the lower deck 8 of the measuring unit 3 there is a lower measurement aperture 13 and in the upper deck 9 an upper measurement aperture 14. The measuring unit has an optics module 15, which may be positioned either above or below the measuring unit. The upper deck additionally has a liquid dispensing unit 16 and a dispensing aperture 17, through which liquids can be dispensed into the wells of the plate 12.

The principal parts of the optics module 15 are a light source unit 18, a mirror unit 19, and a detector unit 20. The optics module is used for directing both excitation light to the sample and emitted light from the sample, from either above or below.

The light source unit 18 has an incandescent bulb 21; an image of the filament of the bulb is converged by means of a lens system 22 to the aperture 24 of an excitation delimiter 23 in the mirror unit 19. It is preferable to keep the bulb switched on only during measuring, in order to increase its useful life.

The excitation light coming from the aperture 24 is collimated using a lens system 25, and the collimated light is directed through a filter 26 to a partly transparent mirror 27. By means of the filter the wavelength of the excitation light is delimited to the desired range.

The light which has passed through the mirror 27 is converged via a focussing lens system 28 to the sample. Thus a spot of light 29 is obtained in a delimited spatial region of the sample.

That portion of the excitation light which is reflected from the mirror 27 is directed to a reference detector 30. By means of it any errors caused in the measurement results by variation in the intensity of the excitation light are compensated for. A representative sample of the excitation light is obtained from the mirror. When one-half of the light is used for excitation, the other half can be exploited for defining the excitation amplitude. A unidirectional beam of light may be directed to a detector having a large surface area or, by means of a converging lens, to a smaller detector.

The light emitted from the spot 29 in the sample travels via the focussing lens system 28 to the lower surface of the mirror 27. From the portion reflected from the mirror, an image of the spot is formed, in the aperture 33 of the emission delimiter 32, by means of a converging lens system 31. From the aperture the emitted light is collimated by means of a lens system 34 to a filter 35, from which it is directed via a converging lens system 36 to a detector 37. By means of the filter, the desired wavelength range is delimited from the emitted light. The filter here is an interference filter. The detector is a photo-multiplier tube.

When the mirror 27 is positioned close to the imaging lens system 28 common to the excitation channel and the emission channel, the image in the mirror is formed at a point far from the object being assayed. When the mirror is at a distance less than the focal distance, no image at all is formed.

The apparatus has a plurality of different excitation filters 26 and emission filters 35. The filters are mounted in a disc, and the desired filter is installed by rotating the disc. The filter discs are also replaceable.

The excitation delimiter 23 is replaceable, and thus an optimal excitation aperture 24 of the desired size and shape can always be placed in the module. The excitation light can thus be focussed, with a good efficiency ratio, precisely on the sample assayed at a given time, or on a preferred or sufficient region thereof. By means of the delimiter it is possible in particular to eliminate disturbances caused by the fluorescence of adjacent samples.

The shape of the delimiting aperture 24 may also vary according to the embodiment. For example, in certain embodiments the fluorescence of an electrophoretically formed line of the sample is to be measured. In such a case, a suitable linear aperture is used.

The user may also, when necessary, visually check the size and shape of the spot of light formed.

The emission delimiter 32 is also replaceable, and thus the light arriving at the detector can be delimited by means of an aperture 33. The light can always be measured from a precisely defined region. This can be used for minimizing background radiation arriving at the detector; such radiation may come in particular from the adjacent wells. The shape of the aperture can also be varied according to the samples to be assayed or their partial regions.

When desired, it is possible to use both an excitation delimiting aperture 24 and an emission delimiting aperture 33 for defining the size and the shape of the measurement region. Often the replacement of only one of the delimiters will suffice, since the disturbing adjacent sample is in any case located outside the area of the wider delimiting aperture. Preferably the excitation light region is made smaller than the emission measurement region.

The emitted light treatment optics described can also be used for eliminating errors caused by variations in the distance to the object being assayed. Such errors may be caused, for example, by curvature of the plate, inclination of the path, and variations in the volume of the samples.

Emission sensitivity can be made constant by making the solid angle of the measurement constant. This is achieved by means of an aperture delimiting parallel rays of light, mounted at a point after the mirror 27. In the embodiment of the figure, the retainer of the lens 31 serves as the delimiter.

By suitable dimensioning, the depth effect can be almost entirely eliminated.

The light source unit 18 is also replaceable. In its place there can be installed against the delimiting aperture 24 the end of an optical fiber bundle by means of which excitation light is directed from an external source of light. In this case the image is formed of the end of the fiber bundle. This arrangement is used, for example, when a Xe bulb is needed, which requires special safety devices. The specific fluorescence of the fiber used for directing light does not cause problems here, since after the fiber the light passes through an excitation filter 26.

A usable partly transparent mirror 27 can be manufactured by forming reflective spots (diameter, for example, approx. 1 mm) on a glass sheet, these spots covering one-half of the optically transparent surface. The reflective material is preferably aluminum, which has a very wide reflection wavelength range (approx. 200 . . . 1500 nm). The glass sheet is preferably as thin as possible, which minimizes the amount of scattered light due to internal reflections in the glass.

Preferably, however, suitably shaped reflective areas are used. The reflective areas of the partly transparent mirror 27.1 in FIG. 3, the reflective areas are made up of a round center 38.1 and of separate radial sectors 39.1 around it, the transparent area 40.1 being respectively cartwheel-shaped. In the mirror according to FIG. 4, for its part, there is a continuous reflective area made up of a cartwheel-shaped center 38.2 and radial sectors 39.2 linked to it of and a transparent area formed by separate radial sectors 40.2. The central area minimizes the internal reflections of the optics. Owing to the edges of the radial reflective areas, diffraction of light can be caused to take place in the direction of a tangent transverse to the radius.

According to one embodiment, the mirror 27.1 or 27.2 is an oval the 45° projection of which is a circle.

In the transfer means 11 according to FIG. 5, the carrier 10 is mounted so as to slide along longitudinal slide bars 41, which in turn are mounted slidably on transverse slide bars 42. The slide bars can be moved by using motors and belts 43 and 44, and thus the carrier can be brought into the desired position within the measuring unit or out of the aperture in the front wall.

The carrier 10 is rectangular, and it has a back wall 45 and side walls 46. In the lower part of the side walls there are supports 47 so that an open space is left in the center. At the ends of the supports there are inward projections. At the front edge the projections have detachable vertical pins 48. The carrier 10 is dimensioned so that the plate for assaying can be placed to bear on the supports 47 so that the bottoms of the wells are left in the area of the opening. If the plate used is smaller than the opening, a suitable adapter tray is first placed to bear on the supports.

One side edge of the carrier 10 has a plate retainer 49. It is a lever having the basic shape of an obtuse V and being pivoted by its apex to a vertical pin 50 in the carrier. To it there is linked a spring 51, one end of which is against the frame of the carrier and the other end against the retainer so that it tends to turn the outer branch of the retainer towards the center of the carrier (in FIG. 5 clockwise). At the end of the outer branch of the retainer there is a projection 52 towards the carrier. When the retainer is in its released state it presses the plate in the carrier against the back wall and that side wall which is opposite the retainer. Thus the plates always settle in the carrier automatically in the same place against the corner. When the carrier is driven out of the measurement apparatus, the inner branch of the retainer impinges against a stop wall 53 in the transfer apparatus, the stop wall forcing the retainer to turn open. Thus a plate can be placed in the carrier or be removed from it. When the pins 48 are detached, a plate can be transferred to the carrier also along a horizontal path.

The back edge of the carrier 10 has four different fluorescent reference surfaces 54, by means of which the sensitivity of the detector can be checked when so desired.

FIG. 6 depicts the dispensing of liquid into a plate 12 in the carrier 10. From the dispensing aperture 17 there enter at an inward slant two dispensing heads 56 and 57. The first can be used for dispensing a liquid into a well in the measuring position and the second for dispensing a liquid into a well adjacent to the measuring position, in particular the one which will arrive next at the measuring position. In addition, the apparatus preferably has a third dispensing head, which can be used for dispensing a liquid into a well transversely adjacent to the measuring position (in FIG. 6 behind the well being measured).

The transfer apparatus 11.1 according to FIG. 7 has a carrier 10.1 movable by means of a belt 43.1 in one direction along slide bar 41.1. The apparatus has a plate retainer 49 similar to that in the apparatus according to FIG. 5.

The transfer apparatus 11.1 according to FIG. 7 can be used, for example, in multichannel photometers in which samples are assayed on a sample plate, such as a microtiter plate 12.1, one row at a time. Respectively the apparatus is suitable for dispensing devices in which liquids are dispensed onto a plate one row at a time.

What is claimed is:

1. An analyzer for measuring optical properties of a sample, which analyzer has a frame in which the sample is placed for measuring and which has an optics module having a detector and optical means for directing light emitted from the sample to the detector, characterized in that; the analyzer comprises a light-tight measuring unit with a lower deck defining a measurement aperture and upper deck defining a measurement aperture, the optics module being positioned alternatively either above the measuring unit, so that light is directed to the detector from above the sample, or below the measuring unit, so that light is directed to the detector from below the sample.

2. An analyser according to claim 1, having a light source for directing light to the sample.

3. An analyser according to claim 2, wherein the light source is in the optics module.

4. An Analyser according to claim 2, wherein the detector and the light source are on the same side of the sample.

5. An analyser according to claim 2 for measuring the fluorescence of a sample.

6. An analyser according to claim 1, having means for directing the light to be measured from a delimited region of the sample to the detector.

7. An analyser according to claim 6, having a converging lens system for forming an image of a delimited region of the sample.

8. An analyser according to claim 7, having a delimiter on which the image of the delimited region of the sample is formed, and means for directing light from the delimiter to the detector.

9. An analyser according to claim 1, having a filter for filtering, at a point before the detector, the light emitted from the sample.

10. An analyser according to claim 1, having means for eliminating the distance variations caused by the object being assayed.

11. An analyser according to claim 1, wherein the sample is in a vessel which has a bottom, side walls and an open mouth.

12. An analyzer according to claim 1, wherein said measuring unit comprises a front wall defining an aperture for transfer of samples into and out of said measuring unit.

13. An analyzer according to claim 1, wherein said measuring unit comprises a movable measuring carrier adapted to receive a plate with samples to be measured.

14. An analyzer according to claim 13, wherein said the upper deck defines a dispensing aperture through which liquids are dispensed.

15. An analyzer for measuring optical properties of a sample, which analyzer has a frame in which the sample is placed for measuring and which has an optics module having a detector and optical means for directing light emitted from the sample to the detector, characterized in that: the analyzer comprises a pivotable measuring unit in which the optics module is positioned alternatively either so that light is directed to the detector from above the sample or so that light is directed to the detector from below the sample.

16. An analyzer according to claim 15, wherein the measuring unit is upwards pivotable.

17. An analyzer according to claim 15, wherein the measuring unit comprises a lower deck with a measurement aperture and an upper deck with a measurement aperture.

18. An analyzer for measuring optical properties of a sample, which analyzer has a frame in which the sample is placed for measuring and which has an optics module having a detector and optical means for directing light emitted from the sample to the detector, characterized in that the analyzer comprises a measuring unit comprising a carrier with a plate for samples to be measured, the carrier sliding along longitudinal slide bars mounted slidably on transverse slide bars, and the optics module being positioned alternatively either so that light is directed to the detector from above the sample or so that light is directed to the detector from below the sample.

19. An analyzer for measuring optical properties of a sample, which analyzer has a frame in which the sample is placed for measuring, an optics module which has a detector and optical means for directing light emitted from the sample to the detector, characterized in that the analyzer has means for directing light to be measured from a delimited spatial region of the sample to the detector, said means for directing light from a delimited spatial region comprising a collimating lens, and the analyzer has means for leading excitation light through the collimating lens.

20. An analyzer according to claim 19, wherein the analyzer further comprises an aperture for delimiting the parallel light coming from the collimating lens.

21. An analyzer according to claim 20, wherein the parallel light from the collimating lens is led to the delimiting aperture by reflecting with a mirror.

22. An analyzer according to claim 21, wherein the mirror is partly transparent.

23. An analyzer according to claim 20, wherein the delimiting aperture is formed by a retainer of a converging lens.

24. An analyzer according to claim 23, wherein the converging lens forms an image of a spot from the sample on another aperture.

25. An analyzer according to claim 24, wherein another aperture is in a replaceable delimiter.

26. An analyzer according to claim 24, wherein light from the other aperture is collimated by means of a lens system and the collimated light led through a filter.

* * * * *